United States Patent
Miyayashiki et al.

(10) Patent No.: US 8,591,401 B2
(45) Date of Patent: Nov. 26, 2013

(54) ENDOSCOPE APPARATUS DISPLAYING INFORMATION INDICATING GRAVITY DIRECTION ON SCREEN

(75) Inventors: Hidehiro Miyayashiki, Akishima (JP); Yoichiro Kasai, Akiruno (JP)

(73) Assignee: Olympus Corporation, Tokyo (JP)

( * ) Notice: Subject to any disclaimer, the term of this patent is extended or adjusted under 35 U.S.C. 154(b) by 135 days.

(21) Appl. No.: 13/210,777

(22) Filed: Aug. 16, 2011

(65) Prior Publication Data

US 2012/0078043 A1    Mar. 29, 2012

(30) Foreign Application Priority Data

Aug. 18, 2010  (JP) ................................. 2010-183378
Nov. 24, 2010  (JP) ................................. 2010-261617

(51) Int. Cl.
*A61B 1/05*    (2006.01)

(52) U.S. Cl.
USPC ............ 600/117; 600/103; 600/109; 600/175

(58) Field of Classification Search
USPC .................. 600/103, 109, 117, 118, 172, 175
See application file for complete search history.

(56) References Cited

U.S. PATENT DOCUMENTS

| | | | | |
|---|---|---|---|---|
| 4,837,626 A | * | 6/1989 | Nishiyama et al. | 348/554 |
| 4,991,957 A | * | 2/1991 | Sakamoto et al. | 356/241.4 |
| 5,179,656 A | * | 1/1993 | Lisle | 715/836 |
| 6,144,382 A | * | 11/2000 | Hill | 345/619 |
| 6,573,896 B1 | * | 6/2003 | Ribadeau Dumas et al. | 345/473 |
| 7,517,314 B2 | * | 4/2009 | Hoeg et al. | 600/117 |
| 8,211,008 B2 | * | 7/2012 | Henzler | 600/109 |
| 2005/0027167 A1 | * | 2/2005 | Chatenever et al. | 600/173 |
| 2005/0272971 A1 | * | 12/2005 | Ohnishi et al. | 600/101 |
| 2006/0084840 A1 | * | 4/2006 | Hoeg et al. | 600/117 |
| 2007/0142705 A1 | * | 6/2007 | Ohnishi et al. | 600/109 |
| 2007/0173694 A1 | * | 7/2007 | Tsuji et al. | 600/146 |

FOREIGN PATENT DOCUMENTS

| | | | | |
|---|---|---|---|---|
| JP | 03037028 A | * | 2/1991 | |
| JP | 03114428 A | * | 5/1991 | |
| JP | 03118019 A | * | 5/1991 | |
| JP | 2002-275257 | | 10/2007 | |

* cited by examiner

*Primary Examiner* — John P Leubecker
(74) *Attorney, Agent, or Firm* — Scully, Scott, Murphy & Presser, P.C.

(57) ABSTRACT

An endoscope apparatus includes an image processing portion for performing image processing on a signal of an image pickup picked up by an image pickup device installed in a distal end portion of an endoscope insertion portion to generate an endoscope image, a gravity direction detecting portion for detecting information about a gravity direction of the distal end portion, a gravity signal processing portion for performing predetermined signal processing on a signal of the information about the detected gravity direction to generate gravity information, a graphics generating portion for generating an indicator indicating the gravity direction based on the gravity information, and an image combining portion for combining the endoscope image and the indicator and outputting combined image information to a display apparatus. The graphics generating portion changes a display form of the indicator indicating the gravity direction according to the gravity direction.

2 Claims, 17 Drawing Sheets

FIG.5
DISPLAY FORM C
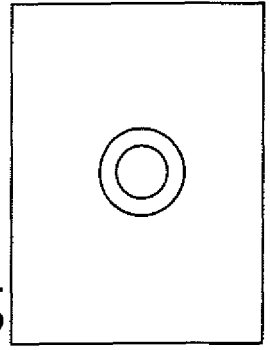
C-1 — PLUMB (STRAIGHT DOWN) DIRECTION
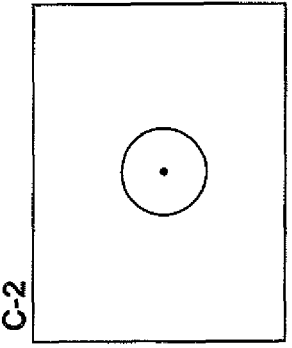
C-2 — VERTICAL (STRAIGHT UP) DIRECTION
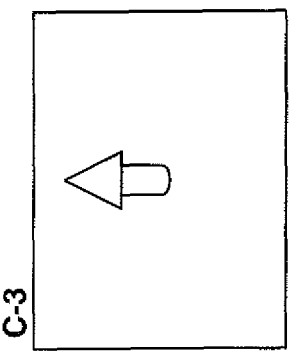
C-3 — SCREEN UP/DOWN DIRECTION
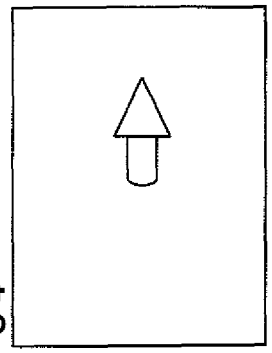
C-4 — SCREEN LEFT/RIGHT DIRECTION

| | FIELD-OF-VIEW DIRECTION FLAG | IMAGE REVERSAL FLAG |
|---|---|---|
| OPTICAL ADAPTER A | DIRECT VIEW | NORMAL IMAGE |
| OPTICAL ADAPTER B | DIRECT VIEW | NORMAL IMAGE |
| OPTICAL ADAPTER C | SIDE VIEW | UPSIDE DOWN ROTATION |
| ⋮ | ⋮ | ⋮ |
| OPTICAL ADAPTER N | SIDE VIEW | LEFT-RIGHT REVERSAL |
| ⋮ | ⋮ | ⋮ |

| | | ROTATION ANGLE WITH AXIS PERPENDICULAR TO LONGITUDINAL DIRECTION AND PARALLEL TO GROUND AS AXIS OF ROTATION [DEGREES] | | | | |
|---|---|---|---|---|---|---|
| | | −90 | −45 | 0 | 45 | 90 |
| ROTATION ANGLE WITH LONGITUDINAL AXIS AS AXIS OF ROTATION [DEGREES] | 0 | 64, 66, 67, 61k, 63, 65 | 64, 66, 67, 61k, 63 | 66, 61k, 63, 64 | 67, 66, 61k, 63, 64 | 65, 67, 66, 61k, 63, 64 |
| | 45 | | | | | |
| | 90 | | | | | |
| | 135 | | | | | |
| | 180 | | | | | |
| | 225 | | | | | |
| | 270 | | | | | |
| | 315 | | | | | |

# ENDOSCOPE APPARATUS DISPLAYING INFORMATION INDICATING GRAVITY DIRECTION ON SCREEN

CROSS REFERENCE TO RELATED APPLICATIONS

This application claims benefit of Japanese Patent Application No. 2010-183378 filed in Japan on Aug. 18, 2010 and 2010-261617 filed in Japan on Nov. 24, 2010, the contents of which are incorporated herein by this reference.

BACKGROUND OF THE INVENTION

1. Field of the Invention

The present invention relates to an endoscope apparatus that displays video with information indicating a gravity direction on a screen.

2. Description of the Related Art

Generally, endoscope apparatuses for displaying endoscope images with information indicating the gravity direction on screens of the display apparatuses have been developed. Display of such a gravity direction gives a reference with respect to which an image pickup surface of an image pickup portion installed in a distal end portion of an endoscope insertion portion (hereinafter, referred to as the endoscope distal end portion or simply the distal end portion) is rotated. Video display of an endoscope that is performed with a plumb (straight down) direction or a vertical (straight up) direction of the gravity direction as a reference is disclosed (for example, see Japanese Patent Application Laid-Open Publication No. 2007-275257).

In endoscope apparatuses that display video with information about a gravity direction on screens, conventionally, an indicator indicating a downward direction of a gravity direction has been continuously displayed on a frame of a video display area and an indicator indicating a gravity direction has been displayed on a part of a display screen (for example, at the bottom right).

In any gravity direction display, when a gravity direction of an endoscope distal end portion is a direction orthogonal to a viewed surface (an image pickup surface), it is difficult for an indicator to express a difference between a plumb (straight down) direction and a vertical (straight up) direction of the distal end portion.

In addition, in recent years, size of display devices such as an LCD has tended to decrease with decreasing size of endoscope systems, but in conventional systems, size of display devices with respect to display of an indicator has not been taken into account.

SUMMARY OF THE INVENTION

An endoscope apparatus of an aspect of the present invention includes: an image processing portion for performing image processing on a signal of an image picked up by an image pickup device installed in a distal end portion of an endoscope insertion portion to generate an endoscope image; a gravity direction detecting portion for detecting information about a gravity direction of the distal end portion; a gravity signal processing portion for performing predetermined signal processing on a signal of the information about the gravity direction detected by the gravity direction detecting portion to generate gravity information; a graphics generating portion for generating an indicator indicating the gravity direction based on the gravity information; and an image combining portion for combining the endoscope image generated by the image processing portion and the indicator generated by the graphics generating portion and outputting combined image information to a display apparatus, and the graphics generating portion changes a display form of the indicator indicating the gravity direction according to the gravity direction.

In addition, an endoscope apparatus of another aspect of the present invention includes a control portion for, according to a position of a distal end portion of an endoscope insertion portion, making an instruction to generate a gravity direction display portion in which at least one of a gravity direction mark indicating a gravity direction and a zenith direction mark indicating a direction opposite to the gravity direction is placed, and the control portion causes, when the position of the distal end portion is changed, at least one of the gravity direction mark and the zenith direction mark to be moved, according to an amount of the change, to a predetermined position of the gravity direction display portion and displayed.

In addition, an endoscope apparatus of yet another aspect of the present invention includes an image processing portion for performing image processing on a signal of an image picked up by an image pickup device installed in a distal end portion of an endoscope insertion portion and generating an endoscope image; a gravity direction display portion in which when the distal end portion is in a normal position, a gravity direction mark indicating a gravity direction and a zenith direction mark indicating a direction opposite to the gravity direction are placed at positions opposing each other on a circumference; a control portion for, according to the position of the distal end portion, making an instruction to generate the gravity direction display portion; and an image combining portion for combining the gravity direction display portion in a predetermined position of the endoscope image, and the control portion causes, when the position of the distal end portion is changed, the gravity direction mark or the zenith direction mark to be moved, according to an amount of the change, to a predetermined position inside the circumference of the gravity direction display portion and displayed.

BRIEF DESCRIPTION OF THE DRAWINGS

FIG. 5 is a diagram illustrating a third display form C of the plurality of types of exemplary display forms of gravity direction displays, the display forms being used in the operation flow of the gravity direction display in FIG. 2;

FIG. 8 is a diagram illustrating an example of optical adapter characteristics stored in an optical adapter characteristics storage portion;

FIG. 15 is a diagram illustrating associations of positions of a distal end of an insertion portion in a direct-view type optical adapter with indicator displays;

FIG. 16 is a diagram illustrating associations of positions of a distal end of an insertion portion in a side-view type optical adapter with indicator displays;

DETAILED DESCRIPTION OF THE PREFERRED EMBODIMENTS

Now, embodiments of the present invention will be described with reference to the drawings.
(First Embodiment)
FIG. 1 is a block diagram illustrating a configuration of an endoscope apparatus according to a first embodiment of the present invention.

Figure 1:
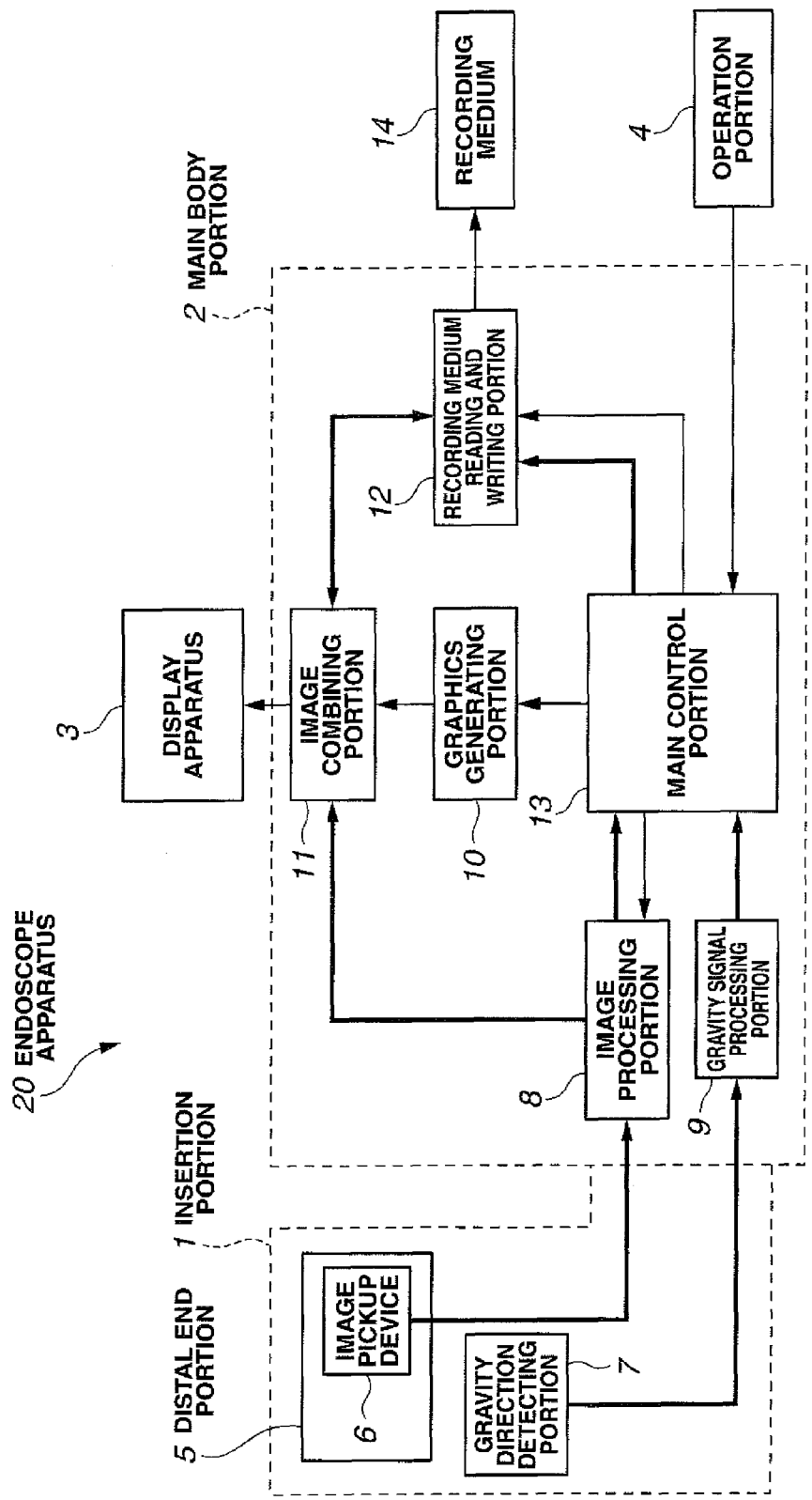
FIG. 1 is a block diagram illustrating a configuration of an endoscope apparatus according to a first embodiment of the present invention.

In FIG. 1, an endoscope apparatus 20 is configured by including an insertion portion 1, a main body portion 2, a display apparatus 3, an operation portion 4, and a recording medium 14.

The insertion portion 1 is composed of a long tubular body that can be inserted into a body cavity, and includes a distal end portion 5, and a gravity direction detecting portion 7.

The distal end portion 5 includes an image pickup device 6 such as a CCD that generates an image pickup signal by performing photoelectric conversion of an object image. The main body portion 2 includes an image processing portion 8, a gravity signal processing portion 9, a graphics generating portion 10, an image combining portion 11, a recording medium reading and writing portion 12, and a main control portion 13.

An image pickup signal outputted from the image pickup device 6 embedded in the distal end portion 5 of the insertion portion 1 is inputted to the image processing portion 8. The image processing portion 8 performs image processing such as gamma correction processing, edge enhancement processing, and digital zoom processing on the image pickup signal to generate an endoscope image. The image processing portion 8 supplies the generated endoscope image to the image combining portion 11.

Also, the insertion portion 1 includes, near a proximal end of the distal end portion 5, the gravity direction detecting portion 7 that detects information about a gravity direction of the distal end portion 5.

The gravity direction detecting portion 7 is, for example, a gravity sensor that uses a triaxial acceleration sensor. The gravity direction detecting portion 7 outputs a signal corresponding to the detected information about the gravity direction of the distal end portion 5, namely, an information signal about the gravity direction of the distal end portion 5, to the gravity signal processing portion 9 of the main body portion 2. It should be noted that the triaxial acceleration sensor can use three sensors in which detection axes of an x axis, a y axis, and a z axis are orthogonal to each other, to obtain magnitude and direction of acceleration in a three-dimensional space, and can combine the obtained magnitude and direction into a vector component to detect direction and magnitude of acceleration of gravity.

The information signal about the gravity direction of the distal end portion 5 outputted from the gravity direction detecting portion 7 is inputted into the gravity signal processing portion 9. The gravity signal processing portion 9 converts the information signal into gravity information representing, for example, an inclination angle with respect to a plumb (straight down) direction or a vertical (straight up) direction, and supplies the converted gravity information to the main control portion 13.

The gravity information is supplied from the main control portion 13 to the graphics generating portion 10. The graphics generating portion 10 generates an indicator indicating a gravity direction based on the gravity information supplied from the main control portion 13 and supplies the generated indicator to the image combining portion 11. The indicator is combined with a moving image and recorded.

The graphics generating portion 10 generates an indicator having a direction varying according to a gravity direction. On the other hand, if the gravity direction of the indicator indicates a predetermined direction (for example, a plumb (straight down) direction or a vertical (straight up) direction), the graphics generating portion 10 changes a display form of the indicator to allow the indicator of the predetermined direction to be more highlighted than indicators of the other directions. For example, for the indicator indicating the gravity direction of the plumb (straight down) direction or the vertical (straight up) direction, a color of the indicator is changed to a color different from a color for the other directions or a shape itself of the indicator is changed into a shape different from a shape for the other directions.

The image combining portion 11 combines the endoscope image supplied from the image processing portion 8 and the indicator supplied from the graphics generating portion 10 into one piece of video data, and outputs the combined synthetic image to the display apparatus 3. Thus, the synthetic image is displayed on the display apparatus 3.

The image combining portion 11 can also perform processing to display an endoscope image exclusively on the display apparatus 3 according to the control by the main control portion 13. Therefore, images such as an endoscope image or a synthetic image of an endoscope image and an indicator are displayed on the display apparatus 3.

A recording medium 14, such as a flash memory card, is detachably connected to the recording medium reading and writing portion 12. In a state in which the recording medium 14 is inserted in the recording medium reading and writing portion 12, if an examiner operates the operation portion 4 to make an instruction to perform a recording operation, the recording medium reading and writing portion 12 reads out, according to control of the main control portion 13, data of an endoscope image and data of gravity information supplied to the image combining portion 11 and supplies the read-out data to the recording medium 14, and the data is recorded on the recording medium 14. In such recording processing, the recording medium reading and writing portion 12 records the data of the endoscope image and the data of the gravity information on the recording medium 14 as one moving image file such as a Motion JPEG format AVI file.

In addition, the recording medium reading and writing portion 12 can read out, according to control of the main control portion 13, data of an endoscope image and data of gravity information recorded on the recording medium 14. At this time, the recording medium reading and writing portion 12 supplies the data of the endoscope image to the image combining portion 11 and supplies the data of the gravity information to the main control portion 13. The data of the gravity information supplied to the main control portion 13 is supplied to the graphics generating portion 10, and an indicator indicating a gravity direction is generated. The indicator indicating the gravity direction is supplied to the image combining portion 11. The image combining portion 11 generates a synthetic image obtained by combining the data of the endoscope image and the data of the indicator. Thus, the synthetic image is displayed on the display apparatus 3.

The operation portion 4 is provided with operation switches, not shown, to perform an operation to bend the distal end portion 5 and a recording operation onto the recording medium 14. The examiner operates the operation switches of the operation portion 4 to perform desired operations such as the bending operation and the recording operation. The operation portion 4 supplies an operation signal corresponding to an examiner operation to the main control portion 13.

The main control portion 13 controls each circuit portion or the like so as to perform the processing according to an operation signal from the operation portion 4 and controls operations of the entire endoscope apparatus 20.

Next, the gravity direction display operation will be described with reference to FIG. 2.

Figure 2:
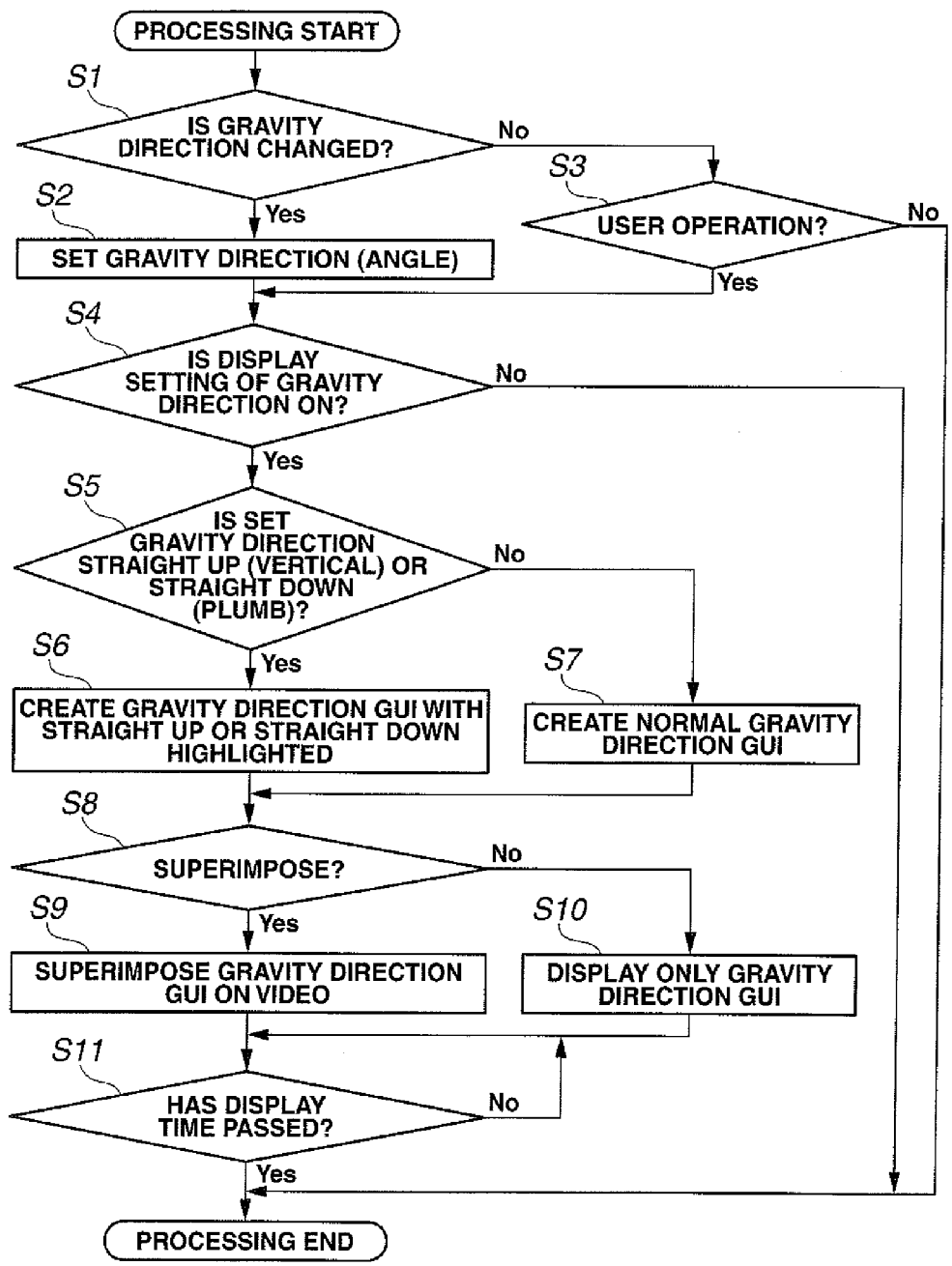
FIG. 2 is a flow chart of an operation to display a gravity direction in FIG. 1.

FIG. 2 is a flow chart of an operation to display a gravity direction in FIG. 1.

If operation processing to display a gravity direction starts, first, the gravity direction detecting portion 7, which is composed of the gravity sensor, determines whether or not the gravity direction is changed (step S1). Note, however, that in order that the gravity sensor detects occurrence of change of the gravity direction, it is necessary that a level of the gravity direction change should exceed a threshold value of sensor sensitivity. Therefore, it is necessary that a threshold value of the gravity direction detecting portion 7 should be set according to sensitivity of the gravity sensor to be used.

If, in step S1, the gravity direction detecting portion 7 detects the occurrence of change of the gravity direction, the gravity direction detecting portion 7 detects a gravity direction (angle) based on a changed amount, and sets the angle to a memory (not shown) in the main control portion 13 (step S2). Then, the processing proceeds to a step S4. In step S1, if the occurrence of change of the gravity direction is not detected, the processing proceeds to a step S3, where it is determined whether or not there is a user operation (step S3).

In step S3, if it is determined that there is an operation, the processing proceeds to the step S4 and if, in step S3, it is not determined that there is an operation, the operation processing of the gravity direction display ends. However, during the operation processing, although not shown, before the operation processing comes to end, the processing continuously or intermittently returns to the first step S1 and re-starts from the step S1.

In step S4, it is checked whether or not a display setting of the gravity direction is ON. If, in step S4, the display setting is ON, it is determined whether the gravity direction set in step S2 is straight up (vertical) or straight down (plumb) (step S5). In step S4, if the display setting is not ON, the operation processing ends.

Then, in step S5, if the gravity direction is straight up (vertical) or straight down (plumb), an arrow of an indicator indicating the gravity direction (hereinafter, sometimes termed the gravity direction GUI) with "straight up (vertical)" or "straight down (plumb)" highlighted (for example, an arrow of a different color) or a display form (mark) different in shape from an arrow is created and displayed (step S6). In step S5, if the gravity direction is not straight up (vertical) or straight down (plumb), an arrow of a normal gravity direction GUI is created (step S7).

After the arrow of the gravity direction GUI is created in step S6 or S7, it is checked whether or not superimposed display of a gravity direction GUI arrow or the like on an endoscope image is set (step S8).

In step S8, if the superimposed display is set, on a screen, the gravity direction GUI arrow or the like is superimposed on the endoscope image (step S9), and if the superimposed display is not set, only the gravity direction GUI arrow or the like is displayed on the screen (step S10).

Then, it is determined whether or not preset display time has passed (step S11). If the display time has not passed, the processing waits the display time to pass, and if the display time has passed, the operation processing ends.

Figure 3:
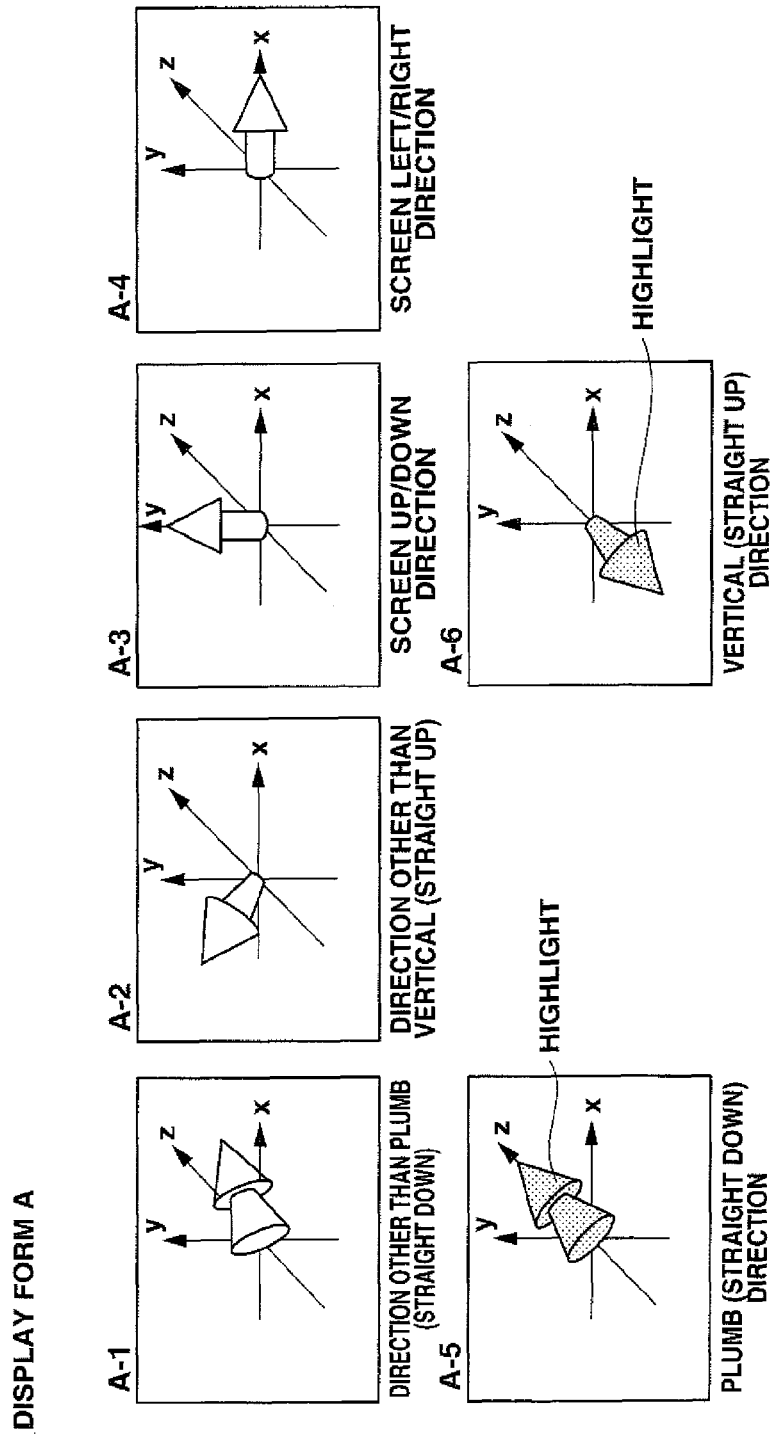
FIG. 3 is a diagram illustrating a first display form A of a plurality of types of exemplary display forms of gravity direction displays, the display forms being used in an operation flow of the gravity direction display in FIG. 2.
Figure 4:
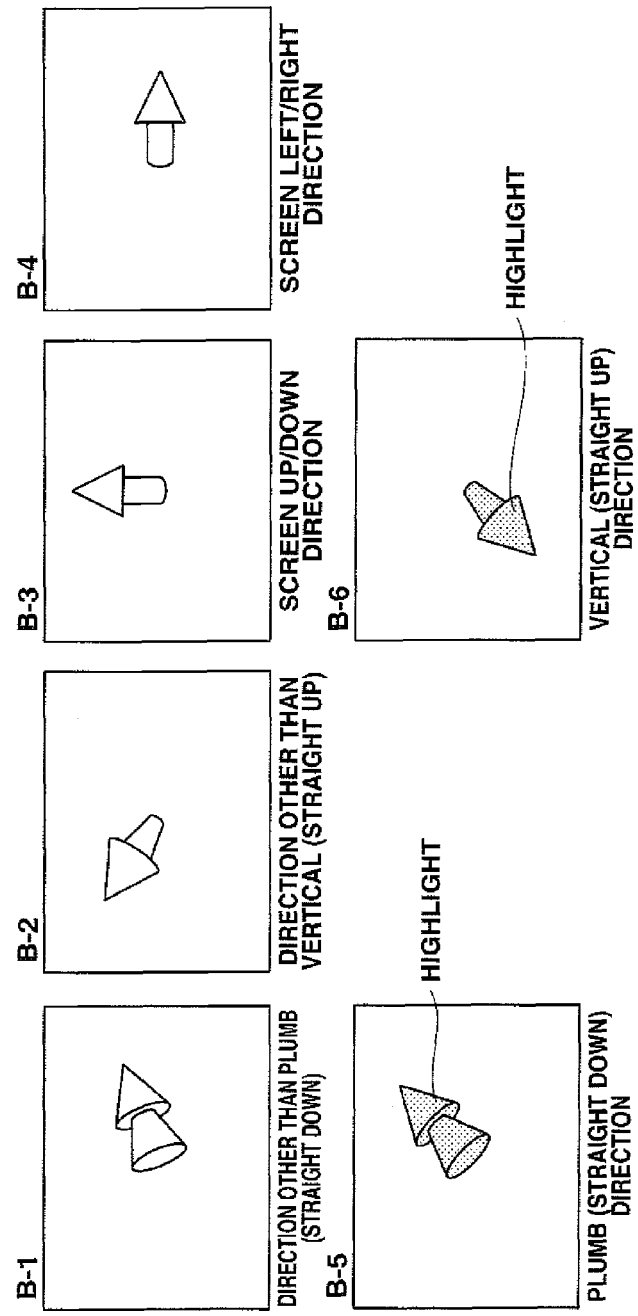
FIG. 4 is a diagram illustrating a second display form B of the plurality of types of exemplary display forms of gravity direction displays, the display forms being used in the operation flow of the gravity direction display in FIG. 2.

FIG. 3 through FIG. 5 illustrate a plurality of (here, three) types of display form examples of the gravity direction display, the display forms being used in the operation flow of the gravity direction display in FIG. 2. Examples of the display forms A and B stereoscopically display indicator arrows for displaying gravity directions. That is, the indicator arrows for indicating gravity directions are stereoscopically displayed in a three-dimensional space that uses three axes of an x axis, a y axis, and a z axis.

FIG. 3 is the first display form A and illustrates patterns with display of three axes. In the x axis, the y axis, and the z axis for representing a three-dimensional space, an insertion direction (an insertion axis direction) of the endoscope distal end portion into a body cavity is associated with (corresponds to) the z axis, and an x-y plane (a plane constituted by the x axis and the y axis) perpendicular to the z axis, which is the insertion axis, is associated with (corresponds to) an image pickup surface (a length-width surface or a width-length surface) of the image pickup device installed in the distal end portion. Here, a direction of an arrow head of the z axis is associated with a plumb (straight down) direction and the x-y plane is associated with a horizontal plane.

In terms of directions of the stereoscopically displayed indicator arrows illustrated in FIG. 3, as representatives of actual situations (directions) of the distal end portion seen when the distal end portion of the endoscope is inserted into a body cavity, six patterns A-1 to A-6 are illustrated in FIG. 3.

The pattern A-1 shows that a gravity direction of the endoscope distal end portion is a direction other than plumb (straight down), the pattern A-2 shows a direction other than vertical (straight up), the pattern A-3 shows a screen up/down direction, the pattern A-4 shows a screen left/right direction, the pattern A-5 shows the plumb (straight down) direction, and the pattern A-6 shows the vertical (straight up) direction.

Here, the indicator arrow of the pattern A-5 representing the plumb (straight down) direction and the indicator arrow of the pattern A-6 representing the vertical (straight up) direction show the case in which the gravity direction coincides with the z axis direction (straight down) or the opposite direction (straight up), so that highlighting the indicator arrow (shown by a dotted pattern in the drawing) by changing a color of the arrow to another such as red allows the operator or the operating person to clearly and easily recognize that the endoscope distal end portion points in the straight down or straight up direction.

FIG. 4 is the second display form B and illustrates the patterns in which triaxial display is removed from the gravity direction display in FIG. 3.

In terms of directions of the stereoscopically displayed indicator arrows illustrated in FIG. 4, as representatives of actual situations (directions) of the distal end portion seen when the distal end portion of the endoscope is inserted into a body cavity, six patterns B-1 to B-6 are illustrated in FIG. 4. The patterns B-1 to B-6 are patterns in which the triaxial display is removed from FIG. 3.

The pattern B-1 shows that a gravity direction of the endoscope distal end portion is a direction other than plumb (straight down), the pattern B-2 shows a direction other than vertical (straight up), the pattern B-3 shows a screen up/down direction, the pattern B-4 shows a screen left/right direction, the pattern B-5 shows the plumb (straight down) direction, and the pattern B-6 shows the vertical (straight up) direction.

Even in the gravity direction display from which the display of the three axes has been removed, since the indicator arrow representing the plumb (straight down) direction of the pattern B-5 and the indicator arrow representing the vertical (straight up) direction of the pattern B-6 are highlighted by, for example, a red color (shown by a dotted pattern in the drawing), the operator or the operating person is allowed to clearly and easily recognize that the endoscope distal end portion points in the straight down or straight up direction.

FIG. 5 is a third display form C and illustrates gravity direction display patterns seen if a gravity direction of the endoscope distal end portion coincides with an axis direction of any one of the three axes, the x axis, the y axis, and the z axis.

In terms of directions of the indicator arrows of the gravity direction display illustrated in FIG. 5, as representatives of actual situations (directions) of the distal end portion seen when the distal end portion of the endoscope is inserted into a body cavity, four patterns C-1 to C-4 are illustrated in FIG. 5.

The pattern C-1 of the display form C shows that a gravity direction is the plumb (straight down) direction and an indicator indicating the gravity direction is represented by a flat mark, a double circle.

The pattern C-2 of the display form C shows that a gravity direction is the vertical (straight up) direction and an indicator indicating the gravity direction is represented by a flat mark composed of a combination of a circle and a point.

The pattern C-3 of the display form C shows that a gravity direction is a screen up/down direction and an indicator is represented by the same mark as used in the pattern A-3 of the display form A or the pattern B-3 of the display form B.

The pattern C-4 of the display form C shows that a gravity direction is a screen left/right direction and an indicator is represented by the same mark as used in the pattern A-4 of the display form A or the pattern B-4 of the display form B.

The third display form C does not include display patterns of directions other than plumb (straight down) direction, vertical (straight up) direction, screen up/down direction, and screen left/right direction. Only if a gravity direction coincides with one of the four directions of the plumb (straight down) direction, the vertical (straight up) direction, the screen up/down direction, and the screen left/right direction, one of the four patterns that is corresponding to the coincidence direction is displayed on the screen. Any one of the display patterns is not three-dimensional stereoscopic display and is two-dimensional flat display.

It should be noted that patterns included in each of the above-described display forms A, B, and C can be variously combined as a new display form group. For example, the patterns A-5 and A-6 of the display form A may be replaced with the patterns C-1 and C-2 of the display form C to create a new display form A' or the patterns B-5 and B-6 of the display form B may be replaced with the patterns C-1 and C-2 of the display form C to create a new display form B'.

In the display forms A and B, the patterns A-5 and A-6 and the patterns B-5 and B-6 are highlighted by changing the color of the patterns. However, if the new display forms A' and B' are used, in the case of the plumb (straight down) direction and the vertical (straight up) direction, since the display form pattern is changed to the display form that is significantly different in shape from the display form of a gravity direction other than the plumb direction or the vertical direction, the user can more definitely identify coincidence between the gravity direction of the endoscope distal end portion and the plumb (straight down) direction or the vertical (straight up) direction.

That is, when the gravity direction coincides with the plumb (straight down) direction or the vertical (straight up) direction, the display of the pattern A-5 or A-6 of the display form A may be shifted to the display of the pattern C-1 or C-2 of the display form C. Similarly, when the gravity direction coincides with the plumb (straight down) direction or the vertical (straight up) direction, the display of the pattern B-5 or B-6 of the display form B may be shifted to the display of the pattern C-1 or C-2 of the display form C.

Figure 6:
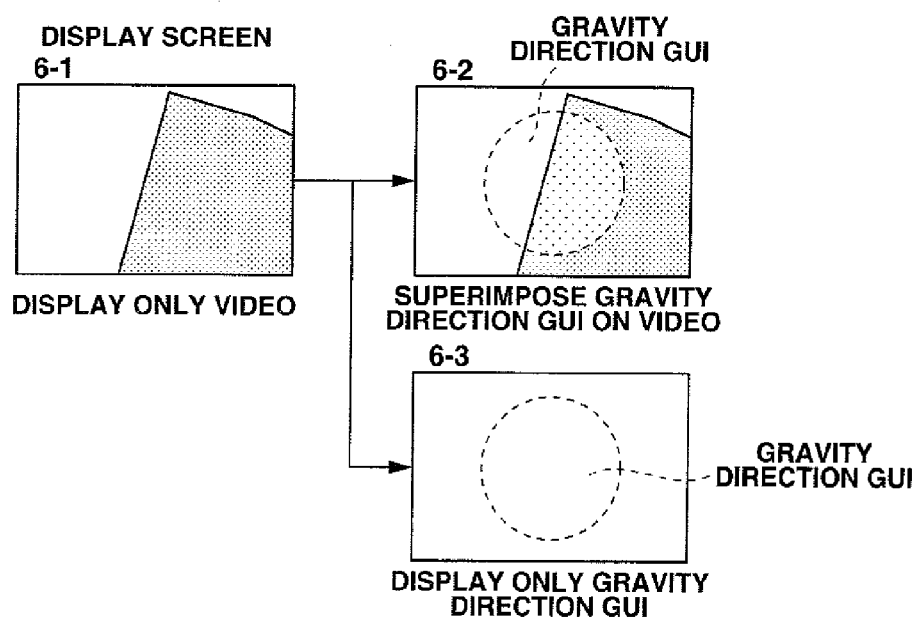
FIG. 6 is a diagram explaining a display operation of a step S9 or a step S10 performed based on a determination of whether or not superimposed display is set in step S8 of the flow in FIG. 2.

FIG. 6 is a diagram explaining a display operation of the step S9 or the step S10 performed based on a determination of whether or not superimposed display is set in step S8 of the flow in FIG. 2.

In the flow shown in FIG. 2, if the superimposed display is set in step S8, a state in which the display apparatus 3 displays an endoscope image (a state denoted by reference numeral 6-1) transitions to a state in which an arrow of a gravity direction GUI (for example, an indicator of the display form illustrated in any one of FIG. 3 to FIG. 5) is superimposed on the endoscope image (a state denoted by reference numeral 6-2). In addition, if the endoscope apparatus does not have a setting of the superimposed display, only the arrow or the like of the gravity direction GUI is independently displayed on the display screen (a state denoted by reference numeral 6-3).

In turning on/off of the superimposed display (set or not set) to superimpose the gravity direction display on video display, a user operation may switch between the screen showing only the video display and the screen showing the superimposed display or the switching between the screen showing only the video display and the screen showing the superimposed display may be performed based on occurrence of a gravity direction change.

In the foregoing embodiment, as a method of, on a display screen, combining and displaying an endoscope image and an indicator indicating a gravity direction of an endoscope distal end portion, a case of superimposing the indicator has been described. However, an area of a display screen may be divided into two parts, and a first display area may display an endoscope image generated by the image processing portion and a second display area may perform two-image parallel display for displaying an indicator indicating a gravity direction. Also, switching between a screen showing only video display and a screen showing two-image parallel display may be performed based on a timing of a user operation or based on a timing at which change of the gravity direction occurs.

According to the foregoing embodiment of the present invention, when video with information indicating a gravity direction is displayed on a screen, an indicator indicating a plumb (straight down) or a vertical (straight up) direction of a gravity direction can be displayed in a manner that the indicator is definitely distinguished from indicators indicating the other directions.

In addition, by switching to the superimposed display in which an indicator indicating a gravity direction is superimposed on an endoscope image, even if a display device is small, the video display is not hampered, and furthermore, a larger size of an indicator can be displayed. Therefore, the user can quickly judge the gravity direction without impairing visibility.

(Second Embodiment)

Next, a second embodiment will be described.

In the second embodiment, an endoscope apparatus that displays an indicator having high visibility of a gravity direction and an opposite gravity direction (a zenith direction) that are three-dimensional will be described.

First, a configuration of the endoscope apparatus according to the second embodiment of the present invention will be described with reference to FIG. 7.

Figure 7:
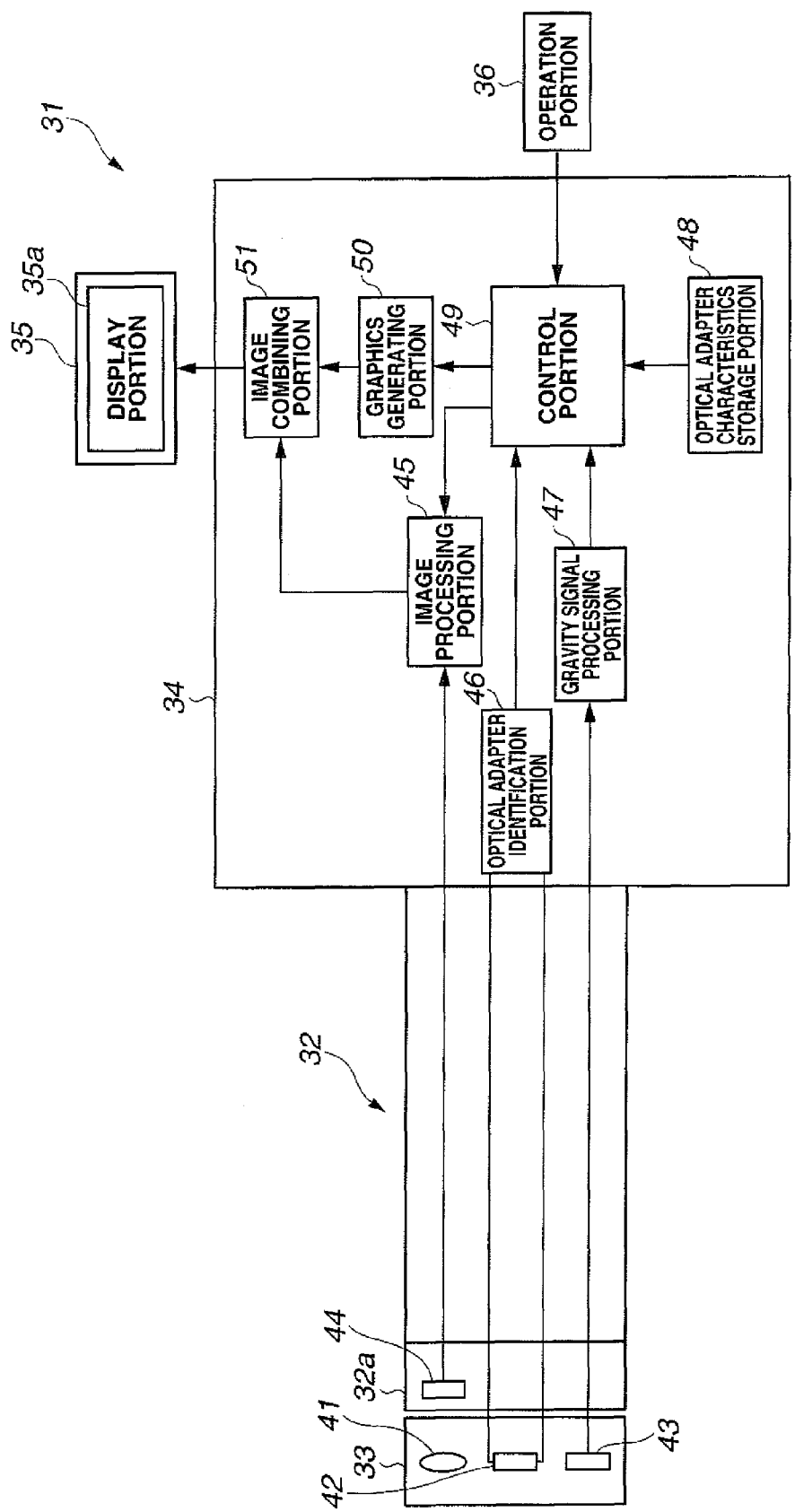
FIG. 7 is a diagram illustrating a configuration of an endoscope apparatus according to a second embodiment of the present invention.

FIG. 7 is a diagram illustrating the configuration of the endoscope apparatus according to the second embodiment of the present invention.

As illustrated in FIG. 7, the endoscope apparatus 31 of the present embodiment is configured by including a long insertion portion 32 having a distal end portion 32a, an exchangeable optical adapter (hereinafter, simply referred to as the optical adapter) 33 detachable with the distal end portion 32a, a main body portion 34, a display apparatus 35 having a display portion 35a, and an operation portion 36 that performs a bending operation to bend the distal end portion 32a in a desired direction.

The optical adapter 33 as a distal end optical system is configured by including an objective lens 41 that picks up an image of an object, an optical adapter identification resistor 42 for identifying a class of the optical adapter 33, and a gravity direction sensing portion 43 that senses a gravity direction of the optical adapter 33.

The gravity direction sensing portion 43 is, for example, a gravity sensor and outputs a signal corresponding to information about the sensed gravity direction of the optical adapter 33, namely, an information signal about the gravity direction of the optical adapter 33, to the main body portion 34.

The distal end portion 32a of the insertion portion 32 is placed at an image forming position of the objective lens 41 and includes an image pickup device 44 such as a CCD that generates an image pickup signal by performing photoelectric conversion of an object image picked up by the objective lens 41. The insertion portion 32 configures an endoscope insertion portion.

The main body portion 34 is configured by including an image processing portion 45, an optical adapter identification portion 46, a gravity signal processing portion 47, an optical adapter characteristics storage portion 48, a control portion 49, a graphics generating portion 50, and an image combining portion 51.

An image pickup signal outputted from the image pickup device 44 embedded in the distal end portion 32a of the insertion portion 32 is inputted to the image processing portion 45. The image processing portion 45 performs image processing such as gamma correction processing, edge enhancement processing, and digital zoom processing on the image pickup signal to generate an endoscope image (an object image). The image processing portion 45 supplies the generated endoscope image to the image combining portion 51.

The optical adapter identification portion 46 as an optical system identification portion detects a resistance value of the optical adapter identification resistor 42 provided with the optical adapter 33 and identifies a class of the optical adapter 33 mounted in the distal end portion 32a. The optical adapter identification portion 46 outputs the identified class of the optical adapter 33 to the control portion 49.

An information signal about the gravity direction of the optical adapter 33 outputted from the gravity direction sensing portion 43 is inputted to the gravity signal processing portion 47. The gravity signal processing portion 47 converts the information signal into gravity information such as an inclination angle with respect to a plumb direction and supplies the converted gravity information to the control portion 49.

The optical adapter characteristics storage portion 48 stores therein optical adapter characteristics according to a class of the optical adapter 33. As illustrated in FIG. 8 described later, the optical adapter characteristics include a field-of-view direction flag and an image reversal flag according to the class of the optical adapter 33.

The control portion 49 detects a gravity direction according to a distal end position of the insertion portion 32 from the gravity information supplied from the gravity signal processing portion 47. The control portion 49 detects, as the gravity direction according to the distal end position of the insertion portion 32, a rotation angle with a longitudinal axis of the insertion portion 32 as an axis of rotation and a rotation angle with an axis perpendicular to the longitudinal direction and parallel to a ground as an axis of rotation.

In addition, the control portion 49 reads out, according to the class of the optical adapter 33 supplied from the optical adapter identification portion 46, associated optical adapter characteristics from the optical adapter characteristics storage portion 48. Then, the control portion 49 corrects, according to the read-out optical adapter characteristics, a coordinate system of the detected gravity direction and supplies the corrected gravity direction information to the graphics generating portion 50. Thereby, the control portion 49 sends an instruction for generating an indicator described later to the graphics generating portion 50.

It should be noted that the optical adapter identification portion 46 has identified a class of the optical adapter 33 according to a resistance value of the optical adapter identification resistor 42, but the user may use the operation portion 36 to select a class of the optical adapter 33. The control portion 49 reads out, according to the class of the optical adapter 33 selected by the operation portion 36, associated optical adapter characteristics from the optical adapter characteristics storage portion 48. According to such a configuration, the optical adapter identification resistor 42 and the optical adapter identification portion 46 can be removed from the endoscope apparatus 31, and thereby the endoscope apparatus 31 can be downsized.

The graphics generating portion 50 generates, based on the gravity direction information supplied from the control portion 49, an indicator indicating a gravity direction and an opposite gravity direction (hereinafter, referred to as the zenith direction) that are three-dimensional and described later, and supplies the generated indicator to the image combining portion 51.

The image combining portion 51 combines the endoscope image supplied from the image processing portion 45 and the indicator supplied from the graphics generating portion 50 and indicating the gravity direction and the zenith direction that are three-dimensional, into one piece of video data, and outputs the combined synthetic image to the display apparatus 35. Thereby, the synthetic image is displayed on the display portion 35a of the display apparatus 35.

In addition, the image combining portion 51 may perform processing to display an endoscope image independently on the display portion 35a of the display apparatus 35 in accordance with control by the control portion 49. Thus, an endoscope image or a synthetic image obtained by combining an endoscope image and an indicator is displayed on the display portion 35a of the display apparatus 35.

Now, the optical adapter characteristics stored in the optical adapter characteristics storage portion will be described.

FIG. 8 is a diagram illustrating an example of the optical adapter characteristics stored in the optical adapter characteristics storage portion.

As illustrated in FIG. 8, in the optical adapter characteristics storage portion 48, as the optical adapter characteristics, a field-of-view direction flag and an image reversal flag are associated with an optical adapter according to a class of the optical adapter. The field-of-view direction flag denotes a field-of-view direction of an associated optical adapter, and the image reversal flag denotes image pickup characteristics of an associated optical adapter.

For example, a field-of-view direction flag of an optical adapter C is side view and an image reversal flag of the optical adapter C is upside-down rotation. Therefore, if the optical adapter 33 mounted in the distal end portion 32a is determined to be the optical adapter C, the optical adapter 33 is a side-view type optical adapter and picks up an upside-down rotated object image.

Next, a rotation angle with a longitudinal axis of the insertion portion 32 as an axis of rotation and a rotation angle with an axis perpendicular to the longitudinal direction and parallel to the ground as an axis of rotation, the angles being detected by the control portion 49, will be described.

Figure 9A:
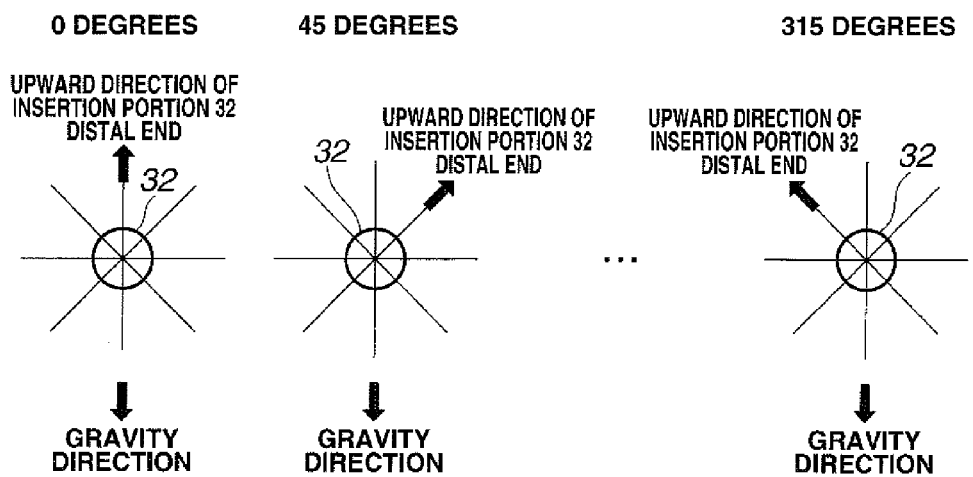
FIG. 9A is a diagram for explaining rotation angles with a longitudinal axis of an insertion portion as an axis of rotation.
Figure 9B:
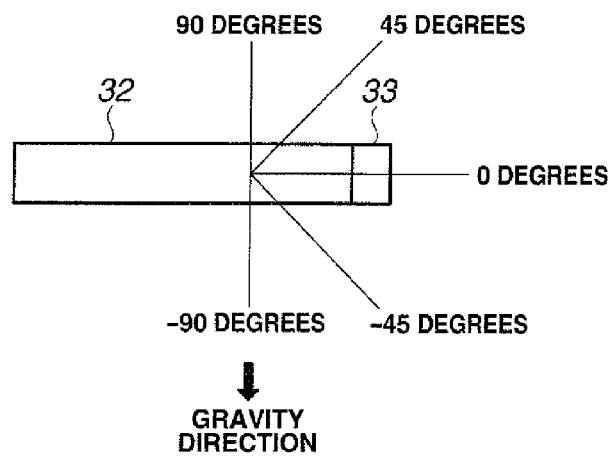
FIG. 9B is a diagram for explaining rotation angles with an axis perpendicular to the longitudinal direction of the insertion portion and parallel to a ground as an axis of rotation.

FIG. 9A is a diagram for explaining the rotation angles with the longitudinal axis of the insertion portion as the axis of rotation. FIG. 9B is a diagram for explaining the rotation angles with the axis perpendicular to the longitudinal direction of the insertion portion and parallel to the ground as the axis of rotation.

The insertion portion 32 illustrated in FIG. 9A has a proximal end side of the insertion portion 32 at a front side of FIG. 9A and a distal end side of the insertion portion 32 at a rear side of FIG. 9A.

As illustrated in FIG. 9A, the control portion 49 detects eight angles of 0, 45, 90, 135, 180, 225, 270, and 315 degrees as the rotation angles with the longitudinal axis of the insertion portion 32 as the axis of rotation. In particular, the control portion 49 detects any one of the eight angles from a rotation range with the longitudinal axis of the insertion portion 32 as the axis of rotation.

For example, if an upward direction of the distal end of the insertion portion 32 is within a rotation range of 22.5 degrees or more and less than 67.5 degrees, the control portion 49 detects that the insertion portion 32 is rotated 45 degrees with the longitudinal axis of the insertion portion 32 as the axis of rotation.

Also, as illustrated in FIG. 9B, the control portion 49 detects five angles of −90, −45, 0, 45, and 90 degrees as the rotation angles with the axis perpendicular to the longitudinal direction of the insertion portion 32 and parallel to the ground as the axis of rotation. In particular, the control portion 49 detects any one of the five angles from a rotation range with the axis perpendicular to the longitudinal direction of the insertion portion 32 and parallel to the ground as the axis of rotation.

For example, if the distal end of the insertion portion 32 is within a rotation range of 22.5 degrees or more and less than 67.5 degrees, the control portion 49 detects that the insertion portion 32 is rotated 45 degrees with the axis perpendicular to the longitudinal direction of the insertion portion 32 and parallel to the ground as the axis of rotation.

It should be noted that the rotation angles with the longitudinal axis of the insertion portion 32 as the axis of rotation and the rotation angles with the axis perpendicular to the longitudinal direction of the insertion portion 32 and parallel to the ground as the axis of rotation are not limited to 45-degree intervals, and may have 30-degree intervals, for example.

Here, correction of a coordinate system of a gravity direction according to optical adapter characteristics will be described.

First, display examples of indicators displayed when correction in a field-of-view direction is performed will be described.

Figure 10A:
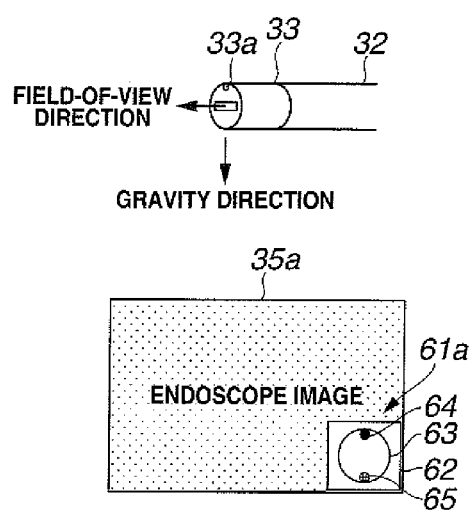
FIG. 10A is a diagram for explaining a display example of an indicator displayed when correction in a field-of-view direction is performed and illustrates an endoscope image picked up by a direct-view type optical adapter.
Figure 10B:
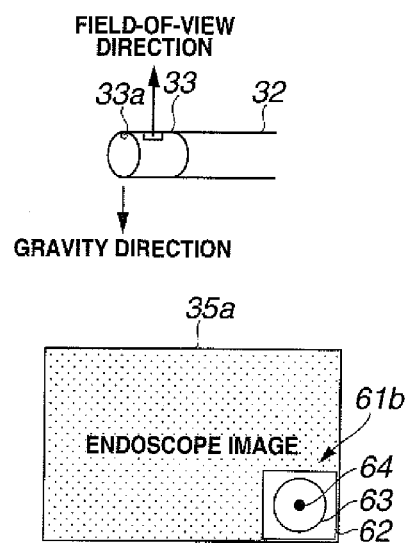
FIG. 10B is a diagram for explaining a display example of an indicator displayed when correction in a field-of-view direction is performed and illustrates an endoscope image picked up by a side-view type optical adapter.

FIG. 10A is a diagram for explaining a display example of an indicator displayed when the correction in the field-of-view direction is performed and illustrates an endoscope image picked up by a direct-view type optical adapter. FIG. 10B is a diagram for explaining a display example of an indicator displayed when correction in a field-of-view direction is performed and illustrates an endoscope image picked up by a side-view type optical adapter.

As illustrated in FIG. 10A, if the optical adapter 33 is a direct-view type optical adapter and an upward direction of the distal end of the insertion portion 32 is a direction opposite to the gravity direction, the graphics generating portion 50 generates an indicator 61a. It should be noted that in FIG. 10A and FIG. 10B, an upward direction mark 33a denoting an upward direction of the distal end of the insertion portion 32 is indicated on the optical adapter 33.

The indicator 61a is composed of a square 62, a circle 63 as a gravity direction display portion included in the square 62, a zenith direction mark 64 included in the circle 63 and indicating a direction opposite to a gravity direction, and a gravity direction mark 65 included in the circle 63 and indicating the gravity direction. It should be noted that the circle 63 as the gravity direction display portion has a configuration that includes the zenith direction mark 64 and the gravity direction mark 65, but a configuration that includes at least one of the zenith direction mark 64 and the gravity direction mark 65 may also be adopted.

If the optical adapter 33 is a direct-view type optical adapter and an upward direction of the distal end of the insertion portion 32 is a direction opposite to the gravity direction, the zenith direction mark 64 is displayed on an upper end of the circle 63 and the gravity direction mark 65 is displayed on a lower end of the circle 63. The zenith direction mark 64 and the gravity direction mark 65 each have different colors so that the user can easily recognize the zenith direction and the gravity direction. It should be noted that the indicator 61a may be transparent. Thereby, an endoscope image area hidden by the indicator 61a can be displayed, so that a flaw or the like of the endoscope image can be prevented from being overlooked.

The indicator 61a is combined at the bottom right of the endoscope image by the image combining portion 51 and is displayed on the display portion 35a of the display apparatus 35.

Now, as illustrated in FIG. 10B, if the optical adapter 33 is a side-view type optical adapter and an upward direction of the distal end of the insertion portion 32 is a direction opposite to the gravity direction, the graphics generating portion 50 generates the indicator 61b. In the indicator 61b, the gravity direction mark 65 is not displayed in the circle 63 and the zenith direction mark 64 is displayed at a center of the circle 63.

Next, display examples of indicators displayed when correction of upside-down rotation is performed will be described.

Figure 11A:
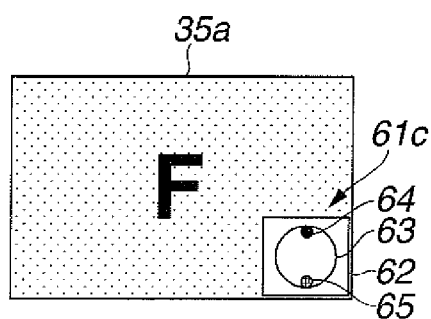
FIG. 11A is a diagram for explaining a display example of an indicator displayed when correction of upside-down rotation is performed and illustrates an endoscope image picked up by an optical adapter with image pickup characteristics of normal image.
Figure 11B:
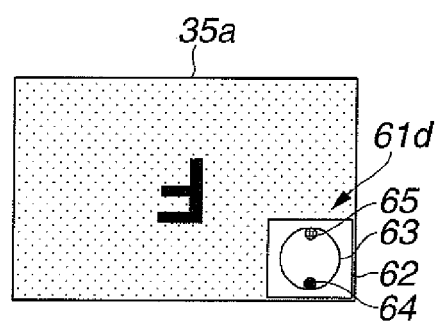
FIG. 11B is a diagram for explaining a display example of an indicator displayed when the correction of upside-down rotation is performed and illustrates an upside-down rotated image obtained by picking up the same object as shown in FIG. 11A by an optical adapter with image pickup characteristics of upside-down rotation.

FIG. 11A is a diagram for explaining a display example of the indicator displayed when the correction of upside-down rotation is performed and illustrates an endoscope image picked up by an optical adapter with image pickup characteristics of normal image. FIG. 11B is a diagram for explaining a display example of the indicator displayed when the correction of upside-down rotation is performed and illustrates an upside-down rotated image obtained by picking up the same object as shown in FIG. 11A by the optical adapter with image pickup characteristics of upside-down rotation. It should be noted that in FIG. 11A and FIG. 11B, the endoscope images are represented by a character "F."

FIG. 11A illustrates the endoscope image picked up by the optical adapter with the image pickup characteristics of normal image. In an indicator 61c of FIG. 11A, the zenith direction mark 64 is displayed on the upper end of the circle 63 and the gravity direction mark 65 is displayed on the lower end of the circle 63.

On the other hand, FIG. 11B illustrates the upside-down rotated image obtained by picking up the same object as shown in FIG. 11A by the optical adapter with the image pickup characteristics of upside-down rotation. In an indicator 61d of FIG. 11B, the gravity direction mark 65 is displayed on the upper end of the circle 63 and the zenith direction mark 64 is displayed on the lower end of the circle 63.

Next, display examples of indicators displayed when correction of left-right reversal is performed will be described.

Figure 12A:
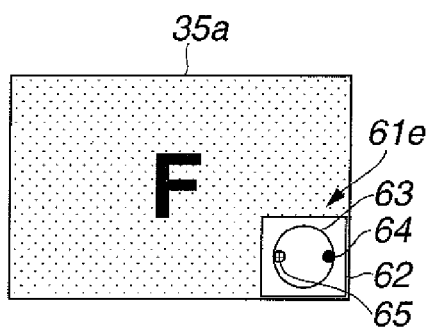
FIG. 12A is a diagram for explaining a display example of an indicator displayed when correction of left-right reversal is performed and illustrates an endoscope image picked up by an optical adapter with image pickup characteristics of normal image.
Figure 12B:
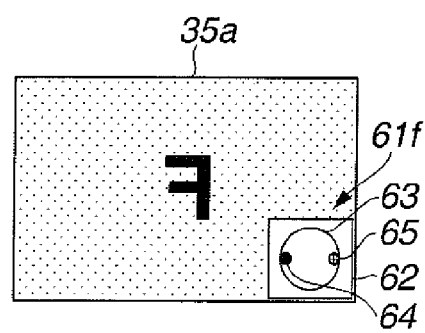
FIG. 12B is a diagram for explaining a display example of an indicator displayed when the correction of left-right reversal is performed and illustrates a left-right reversed image obtained by picking up the same object as shown in FIG. 12A by an optical adapter with image pickup characteristics of left-right (mirror) reversal.

FIG. 12A is a diagram for explaining a display example of the indicator displayed when the correction of left-right reversal is performed and illustrates an endoscope image picked up by an optical adapter with image pickup characteristics of normal image. FIG. 12B is a diagram for explaining a display example of the indicator displayed when the correction of left-right reversal is performed and illustrates a left-right reversed image obtained by picking up the same object as shown in FIG. 12A by an optical adapter with image pickup characteristics of left-right (mirror) reversal.

FIG. 12A illustrates the endoscope image picked up by the optical adapter with the image pickup characteristics of normal image. In an indicator 61e of FIG. 12A, the zenith direction mark 64 is displayed on a right end of the circle 63 and the gravity direction mark 65 is displayed on a left end of the circle 63.

On the other hand, FIG. 12B illustrates the left-right reversed image obtained by picking up the same object as shown in FIG. 12A by the optical adapter with the image pickup characteristics of left-right (mirror) reversal. In an indicator 61f of FIG. 12B, the zenith direction mark 64 is displayed on the left end of the circle 63 and the gravity direction mark 65 is displayed on the right end of the circle 63.

Figure 13:
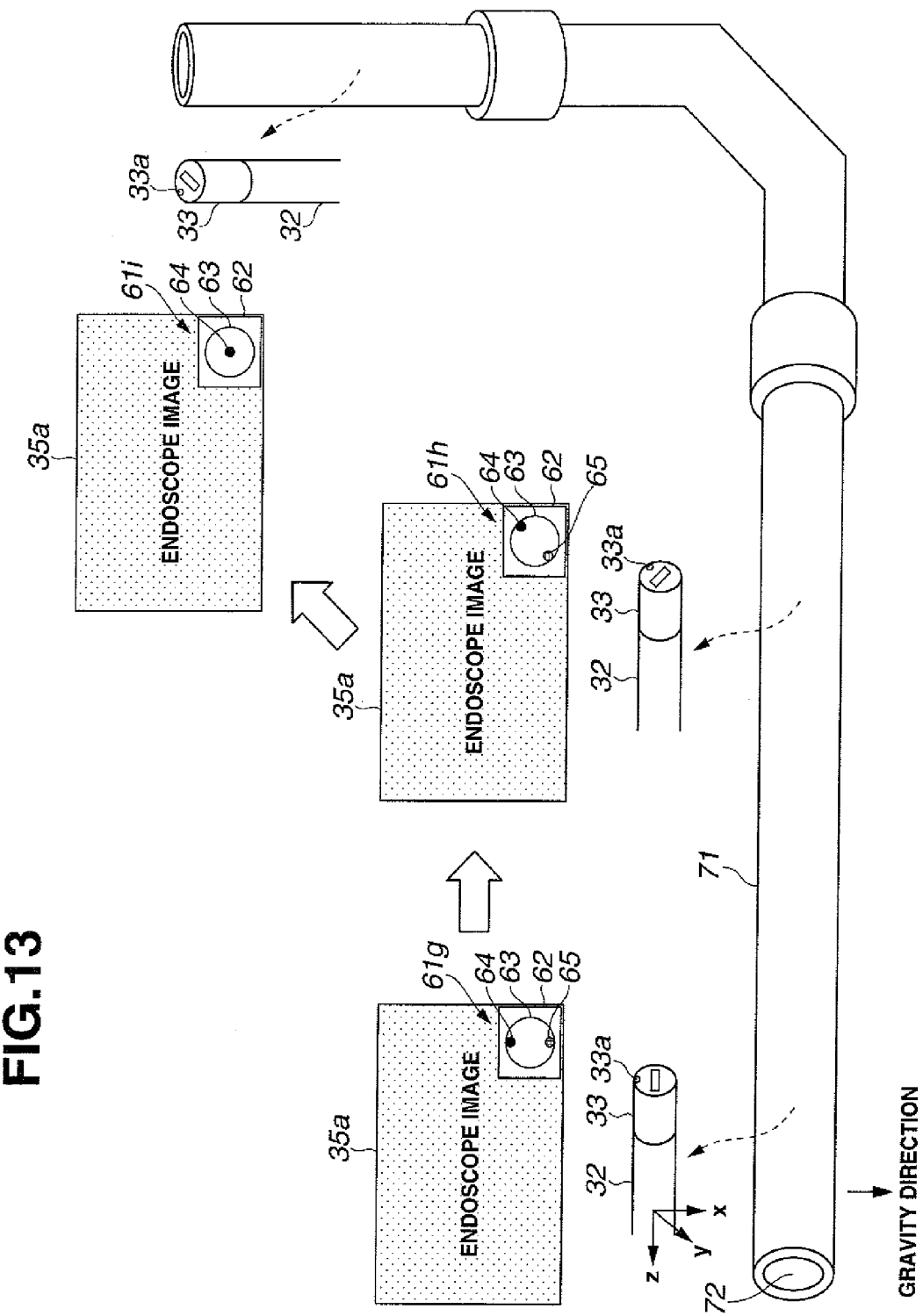
FIG. 13 is a diagram for explaining associations of positions of an insertion portion with displays of an indicator in an examination.

FIG. 13 is a diagram for explaining associations of positions of an insertion portion with displays of an indicator in an examination.

If the insertion portion 32 is inserted into a pipe 71 in a plant as a subject to examine the pipe, a user inserts the insertion portion 32 into an entrance 72 of the pipe 71. If each of the rotation angle with the longitudinal axis of the insertion portion 32 as the axis of rotation and the rotation angle with the axis perpendicular to the longitudinal direction and parallel to the ground as the axis of rotation is 0 degrees, in an indicator 61g, the zenith direction mark 64 is displayed on the upper end of the circle 63 and the gravity direction mark 65 is displayed on the lower end of the circle 63.

When the long insertion portion 32 is further inserted into the pipe 71, if the insertion portion 32 is rotated 45 degrees with the longitudinal axis (in FIG. 13, the z axis) of the insertion portion 32 as an axis of rotation, in an indicator 61h, the zenith direction mark 64 is displayed on an upper-right end of the circle 63 and the gravity direction mark 65 is displayed on a lower-left end of the circle 63.

When the long insertion portion 32 is further inserted into the pipe 71, if the insertion portion 32 is turned straight up with respect to the gravity direction due to a bend of the pipe 71, that is, if an rotation angle with the axis perpendicular to the longitudinal direction and parallel to the ground as the axis of rotation is 90 degrees, in an indicator 61i, the zenith direction mark 64 is displayed on the center of the circle 63.

Figure 14A:
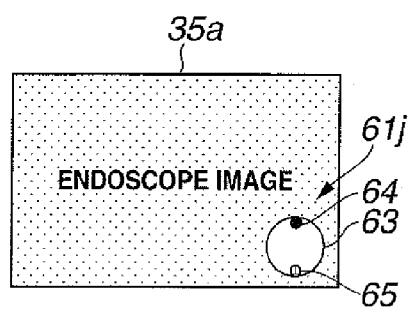
FIG. 14A is a diagram illustrating another display example of the indicator.
Figure 14B:
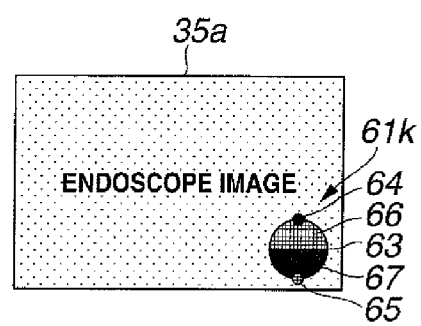
FIG. 14B is a diagram illustrating yet another display example of the indicator.

FIG. 14A and FIG. 14B are diagrams illustrating other display examples of indicators.

In the indicator 61j of FIG. 14A, the square 62 of the indicator 61a of FIG. 10A has been removed. Thereby, the viewed area of the endoscope image is increased, so that a flaw or the like can be prevented from being overlooked.

In the indicator 61k of FIG. 14B, the zenith direction mark 64 and the gravity direction mark 65 are placed at positions opposing each other on a circumference of the circle 63. In addition, in the indicator 61k, a zenith direction area 66 and a gravity direction area 67 are placed inside the circle 63. The zenith direction area 66 and the gravity direction area 67 are classified by different colors. The zenith direction area 66 has, for example, a color of blue, which represents sky and the gravity direction area 67 has, for example, a color of brown, which represents ground. The display areas of the zenith direction area 66 and the gravity direction area 67 are modified according to positions of the distal end of the insertion portion 32. Thereby, the user can easily distinguish the zenith direction from the gravity direction.

It should be noted that the circle 63 as the gravity direction display portions in FIG. 14A and FIG. 14B is not limited to the circle shape and may be, for example, a quadrangle or an octagon.

Now, associations of positions of the distal end of the insertion portion 32 with indicator displays will be described.

First, associations of positions of a distal end of an insertion portion in a direct-view type optical adapter with indicator displays will be described.

Figure 15:
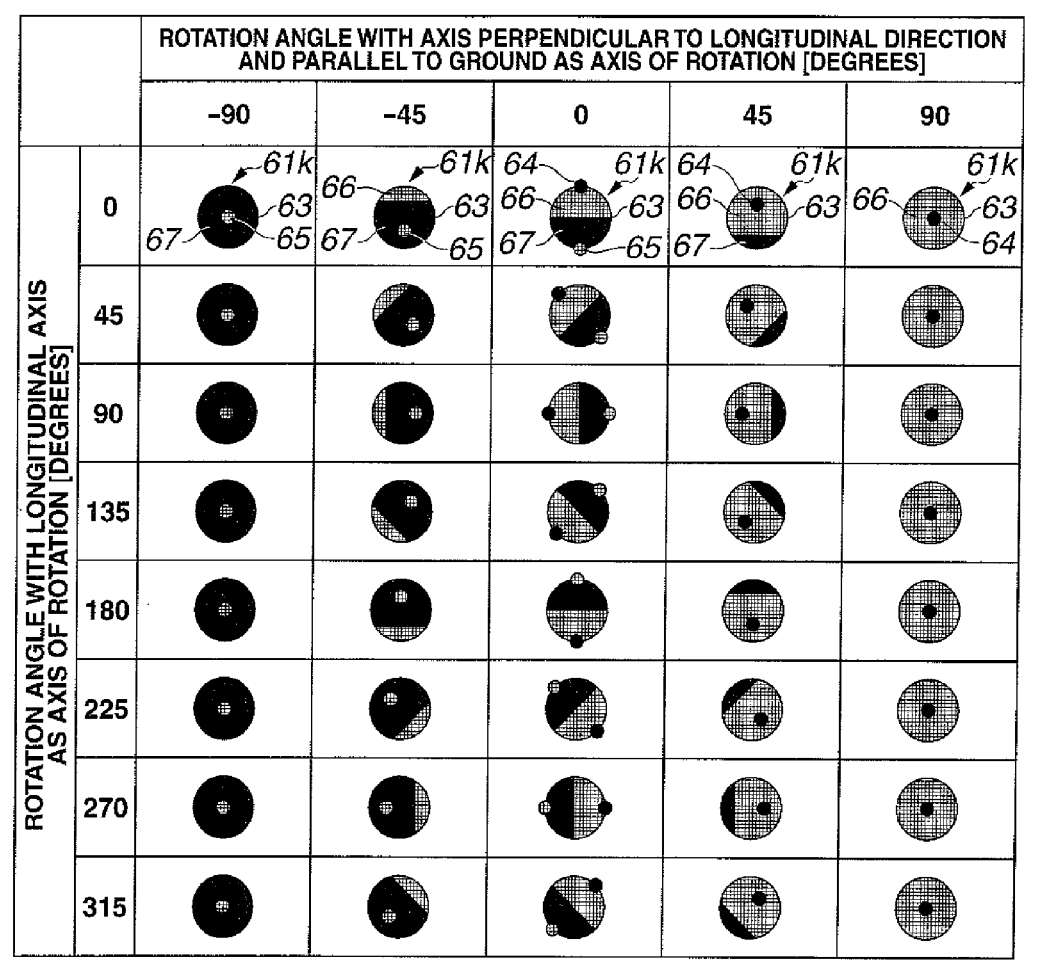

FIG. 15 is a diagram illustrating the associations of the positions of the distal end of the insertion portion in the direct-view type optical adapter with the indicator displays. It should be noted that an indicator in FIG. 15 is explained by taking the indicator 61k shown in FIG. 14B as an example. In addition, to simplify explanation, only when the rotation angle with the longitudinal axis as the axis of rotation is 0 degrees, reference numerals are attached.

As illustrated in FIG. 15, the indicator 61k generated by the graphics generating portion 50 is classified into 40 types according to the rotation angles with the longitudinal axis as the axis of rotation and the rotation angles with the axis perpendicular to the longitudinal direction and parallel to the ground as the axis of rotation. However, if the rotation angle with the axis perpendicular to the longitudinal direction and parallel to the ground as the axis of rotation is −90 and 90 degrees, regardless of the rotation angles with the longitudinal axis as the axis of rotation, the number of each type of the indicator 61k is one. Therefore, accurately, the number of types of the indicator 61k is 26.

If each of the rotation angle with the longitudinal axis as the axis of rotation and the rotation angle with the axis perpendicular to the longitudinal direction and parallel to the ground as the axis of rotation is 0 degrees, the zenith direction mark 64 and the gravity direction mark 65 are placed on the circumference of the circle 63. The zenith direction area 66 is displayed in an upper part being substantially ½ of the circle 63 and the gravity direction area 67 is displayed in a lower part being substantially ½ of the circle 63.

In addition, when the rotation angle with the longitudinal axis as the axis of rotation is 0 degrees and the rotation angle with the axis perpendicular to the longitudinal direction and parallel to the ground as the axis of rotation becomes 45 degrees, the zenith direction mark 64 moves from the circumference of the circle 63 to the inside and is placed at the substantially midway point between the upper end and the center of the circle 63. The zenith direction area 66 is displayed in an upper part being substantially ⅔ of the circle 63 and the gravity direction area 67 is displayed in a lower part being substantially ⅓ of the circle 63.

Furthermore, when the rotation angle with the longitudinal axis as the axis of rotation is 0 degrees and the rotation angle with the axis perpendicular to the longitudinal direction and parallel to the ground as the axis of rotation becomes 90 degrees, the zenith direction mark 64 is placed at the center of the circle 63. The zenith direction area 66 is displayed on the entire of the circle 63.

Similarly, when the rotation angle with the longitudinal axis as the axis of rotation is 0 degrees and the rotation angle with the axis perpendicular to the longitudinal direction and parallel to the ground as the axis of rotation becomes −45 degrees, the gravity direction mark 65 moves from the circumference of the circle 63 to the inside and is placed at the substantially midway point between the lower end and the center of the circle 63. The zenith direction area 66 is displayed in an upper part being substantially ⅓ of the circle 63 and the gravity direction area 67 is displayed in a lower part being substantially ⅔ of the circle 63.

Furthermore, when the rotation angle with the longitudinal axis as the axis of rotation is 0 degrees and the rotation angle with the axis perpendicular to the longitudinal direction and parallel to the ground as the axis of rotation becomes −90 degrees, the gravity direction mark 65 is placed at the center of the circle 63. The gravity direction area 67 is displayed on the entire of the circle 63.

Next, associations of positions of a distal end of an insertion portion in a side-view type optical adapter and indicator displays will be described.

FIG. 16 is a diagram illustrating the associations of the positions of the distal end of the insertion portion in the side-view type optical adapter with the indicator displays.

If each of the rotation angle with the longitudinal axis as the axis of rotation and the rotation angle with the axis perpendicular to the longitudinal direction and parallel to the ground as the axis of rotation is 0 degrees, the zenith direction mark 64 is placed at the center of the circle 63. The zenith direction area 66 is displayed on the entire of the circle 63.

In addition, when the rotation angle with the longitudinal axis as the axis of rotation is 0 degrees and the rotation angle with the axis perpendicular to the longitudinal direction and parallel to the ground as the axis of rotation becomes 45 degrees, the zenith direction mark 64 is placed at the substantially midway point between the lower end and the center of the circle 63. The zenith direction area 66 is displayed in the lower part being substantially ⅔ of the circle 63 and the gravity direction area 67 is displayed in the upper part being substantially ⅓ of the circle 63.

Furthermore, when the rotation angle with the longitudinal axis as the axis of rotation is 0 degrees and the rotation angle with the axis perpendicular to the longitudinal direction and parallel to the ground as the axis of rotation becomes 90 degrees, the zenith direction mark 64 is placed on the lower end of the circumference of the circle 63 and the gravity direction mark 65 is placed on the upper end of the circumference of the circle 63. The zenith direction area 66 is displayed in the lower part being substantially ½ of the circle 63 and the gravity direction area 67 is displayed in the upper part being substantially ½ of the circle 63.

Similarly, when the rotation angle with the longitudinal axis as the axis of rotation is 0 degrees and the rotation angle with the axis perpendicular to the longitudinal direction and parallel to the ground as the axis of rotation becomes −45 degrees, the zenith direction mark 64 is placed at the substantially midway point between the upper end and the center of the circle 63. The zenith direction area 66 is displayed in the upper part being substantially ⅔ of the circle 63 and the gravity direction area 67 is displayed in the lower part being substantially ⅓ of the circle 63.

Furthermore, when the rotation angle with the longitudinal axis as the axis of rotation is 0 degrees and the rotation angle with the axis perpendicular to the longitudinal direction and parallel to the ground as the axis of rotation becomes −90 degrees, the gravity direction mark 65 is placed at the center of the circle 63. The zenith direction mark 64 is placed on the upper end of the circumference of the circle 63 and the gravity direction mark 65 is placed on the lower end of the circumference of the circle 63. The zenith direction area 66 is displayed in the upper part being substantially ½ of the circle 63 and the gravity direction area 67 is displayed in the lower part being substantially ½ of the circle 63.

It should be noted that the indicators illustrated in FIG. 15 and FIG. 16 may be stored in a storage portion, not shown. Then, the control portion 49 reads out an indicator according to the class of the optical adapter 33 and the gravity direction based on the distal end position of the insertion portion 32 from the storage portion, not shown, and outputs the indicator to the image combining portion 51. The indicators illustrated in FIG. 15 and FIG. 16 are generated by the graphics generating portion 50 based on an instruction of the control portion 49, but if the indicators are stored in the storage portion, not shown, and the control portion 49 reads out the indicators, the graphics generating portion 50 can be removed from the endoscope apparatus 31, and thereby the endoscope apparatus 31 can be downsized.

Now, processing to display a gravity direction on a screen performed by the endoscope apparatus 31 configured as such will be described.

Figure 17:
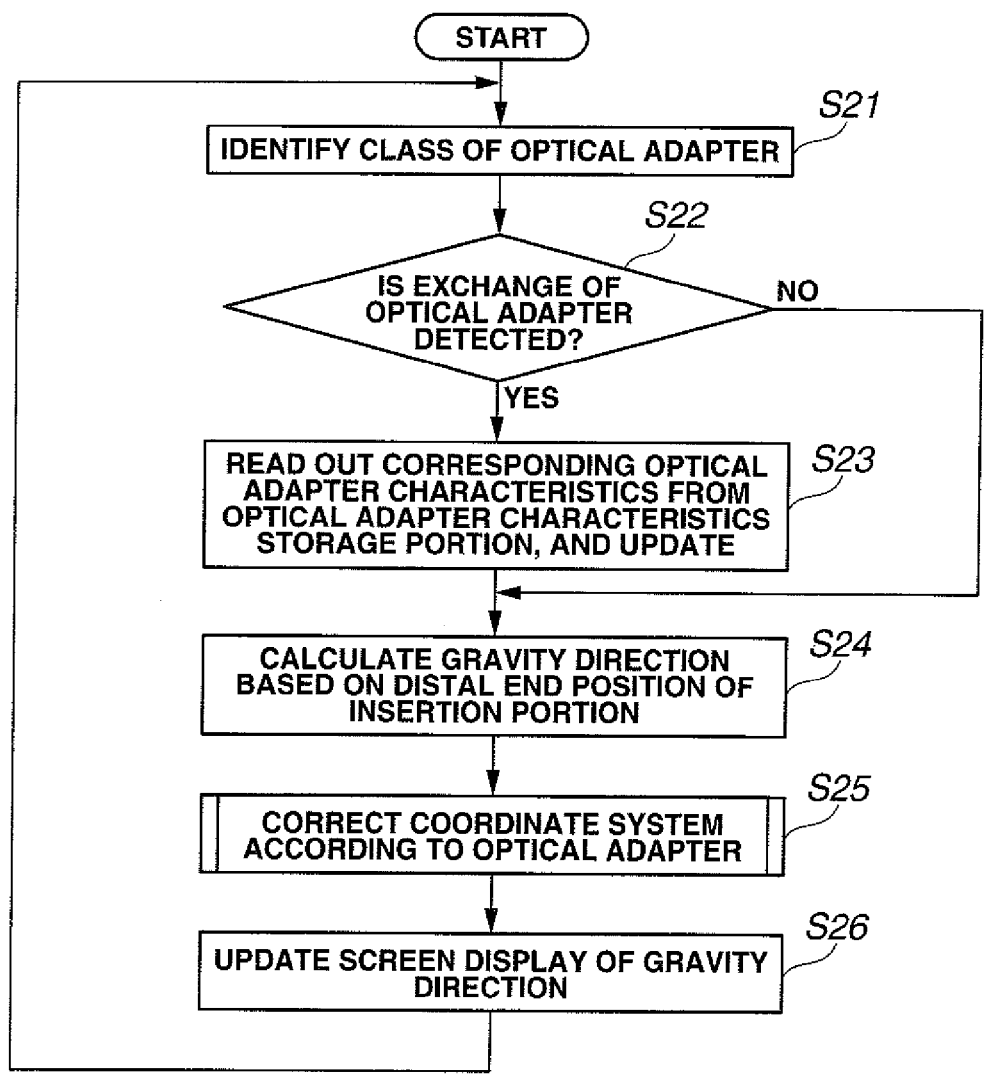
FIG. 17 is a flow chart for explaining an example of processing to display a gravity direction on a screen.

FIG. 17 is a flow chart for explaining an example of the processing to display a gravity direction on the screen.

First, a class of an optical adapter is identified (step S21). Then, it is detected whether or not exchange of the optical adapter has been performed (step S22). If it is detected that the exchange of the optical adapter has not been performed (NO in step S22), the processing proceeds to a step S24. On the other hand, if it is detected that the exchange of the optical adapter has been performed, optical adapter characteristics associated with the changed optical adapter are read out from the optical adapter characteristics storage portion and optical adapter characteristics are updated (step S23). A gravity direction based on a distal end position of the insertion portion is calculated (step S24). Next, a coordinate system is corrected according to the optical adapter (step S25). Finally, a screen display of the gravity direction is changed (step S26). If the processing in step S26 ends, the processing returns to the step S21, and the same processing is repeated.

Next, the processing to correct a coordinate system in step S25 will be described.

Figure 18:
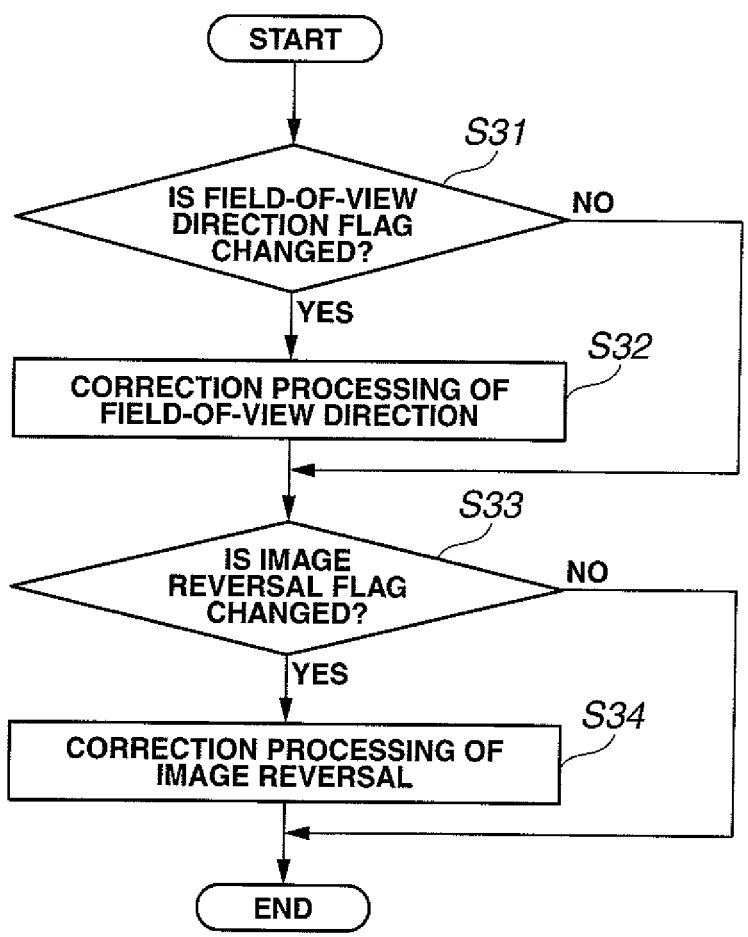
FIG. 18 is a flow chart for explaining an example of processing to correct a coordinate system in step S25 of FIG. 17.

FIG. 18 is a flow chart for explaining an example of the processing to correct the coordinate system in step S25 of FIG. 17.

First, it is detected whether or not the field-of-view direction flag has been changed (step S31). If the field-of-view direction flag has not been changed (NO in step S31), the processing proceeds to step S33. On the other hand, if the field-of-view direction flag has been changed (YES in step S31), correction processing of the field-of-view direction is performed (step S32). Next, it is detected whether or not the image reversal flag has been changed (step S33). If the image reversal flag has not been changed (NO in step S33), the processing ends. On the other hand, if the image reversal flag has been changed (YES in step S33), correction processing of the image reversal is performed (step S34), and the processing ends.

As described above, if the position of the distal end of the insertion portion 32 is in a normal position, that is, here, if each of the rotation angle with the longitudinal axis as the axis of rotation and the rotation angle with the axis perpendicular to the longitudinal direction and parallel as the axis of rotation is 0 degrees, the endoscope apparatus 31 places the zenith direction mark 64 and the gravity direction mark 65 respectively on the upper end and the lower end of the circumference of the circle 63. Then, if the position of the distal end of the insertion portion 32 has been changed, the endoscope apparatus 31 calculates a rotation angle with the longitudinal axis as the axis of rotation and a rotation angle with the axis perpendicular to the longitudinal direction and parallel as the axis of rotation, and causes, according to the rotation angle, the zenith direction mark 64 or the gravity direction mark 65 to be moved to a predetermined position on the circumference of the circle 63 and displayed.

Alternatively, the endoscope apparatus 31 causes, according to the rotation angle, the zenith direction mark 64 or the gravity direction mark 65 to be moved to a predetermined position inside the circle 63 and displayed. As a result, for example, if the rotation angle with the longitudinal axis as the axis of rotation is 0 degrees and the rotation angle with the axis perpendicular to the longitudinal direction and parallel as the axis of rotation is 90 degrees, the zenith direction mark 64 is displayed at a center position inside the circle 63 of the indicator 61k according to the rotation angle.

Thus, according to the endoscope apparatus of the present embodiment, an indicator having high visibility of a gravity direction and an opposite gravity direction (a zenith direction) that are three-dimensional can be displayed.

It should be noted that the steps of each flow chart herein may be executed in different order, some of the steps may be executed at the same time, or the steps may be executed in different order every time, unless such modifications are contrary to the nature of the processing.

The present invention is not limited to the above-described embodiments, and a variety of variations and modifications can be made without changing the gist of the present invention.

What is claimed is:

1. An endoscope apparatus comprising:
   an image processing portion for performing image processing on a signal of an image picked up by an image pickup device installed in a distal end portion of an endoscope insertion portion and generating an endoscope image;
   a graphics generating portion for generating a gravity direction graphic to be displayed with the endoscope image in which when the distal end portion is in a normal position, a gravity direction mark indicating a gravity direction and a zenith direction mark indicating a direction opposite to the gravity direction are placed at positions opposing each other on a circumference of the gravity direction graphic;
   a control portion for, according to the position of the distal end portion, controlling the graphics generating portion to generate the gravity direction graphic;
   an image combining portion for combining the gravity direction graphic in a predetermined position of the endoscope image;
   a distal end optical system that is detachably attached to the distal end portion, the distal end optical system comprising an identification portion; and
   an optical system identification portion for identifying a class of the distal end optical system based on the identification portion,
   wherein the control portion
      causes, when the position of the distal end portion is changed, the gravity direction mark or the zenith direction mark to be moved, according to an amount of the change, to a predetermined position inside the circumference of the gravity direction graphic and to be displayed, and
      corrects a coordinate system of the gravity direction mark and the zenith direction mark based on the class of the distal end optical system identified by the optical system identification portion, and makes an instruction to generate the gravity direction graphic in which the gravity direction mark and the zenith direction mark of the corrected coordinate system are placed.

2. The endoscope apparatus according to claim 1, wherein the distal end optical system comprises an identification resistor that serves as the identification portion, and the optical system identification portion identifies the class of the distal end optical system based on the resistor of the identification resistor.

\* \* \* \* \*